(12) United States Patent
Lackie et al.

(10) Patent No.: US 6,664,114 B1
(45) Date of Patent: *Dec. 16, 2003

(54) SOLID PHASE ASSAY FOR DETECTION OF LIGANDS

(75) Inventors: Steve J. Lackie, Boise, ID (US); Thomas R. Glass, Idaho City, ID (US)

(73) Assignee: Sapidyne Instruments, Inc., Boise, ID (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/277,225

(22) Filed: Jul. 18, 1994

Related U.S. Application Data

(63) Continuation-in-part of application No. 08/262,741, filed on Jun. 20, 1994, now abandoned, which is a continuation of application No. 08/197,431, filed on Feb. 16, 1994, now abandoned, which is a continuation-in-part of application No. 07/924,720, filed on Aug. 3, 1992, now Pat. No. 5,372,783.

(51) Int. Cl.⁷ .......................................... G01N 33/543
(52) U.S. Cl. ........................ 436/518; 435/7.1; 435/7.92; 435/7.95; 435/962; 435/967; 436/514; 436/523; 436/538; 422/55; 422/56; 422/57
(58) Field of Search .................. 435/7.1, 7.92–7.95, 435/962, 967; 436/523, 538, 518; 422/55–57

(56) References Cited

U.S. PATENT DOCUMENTS

| | | |
|---|---|---|
| 1,716,321 A | 6/1929 | Pearson |
| 2,798,718 A | 7/1957 | Gross |
| 3,002,092 A | 9/1961 | Cary |
| 3,025,142 A | 3/1962 | Williams |
| 3,492,396 A | 1/1970 | Dalton et al. |
| 3,600,063 A | 8/1971 | Bowen |
| 3,740,552 A | 6/1973 | Pressman |
| 4,059,685 A | 11/1977 | Johnson |
| 4,153,675 A | 5/1979 | Klelnerman |
| 4,173,392 A | 11/1979 | Ekinaka et al. |
| 4,268,171 A | 5/1981 | Sternberg |
| 4,425,438 A | 1/1984 | Bauman et al. |
| 4,434,236 A | 2/1984 | Freytag |
| 4,454,234 A | 6/1984 | Czerlinski |
| 4,469,787 A | 9/1984 | Woods et al. |
| 4,505,260 A | 3/1985 | Metzger |
| 4,582,809 A | 4/1986 | Block et al. |
| 4,585,623 A | 4/1986 | Chandler |
| 4,652,533 A | 3/1987 | Jolley |
| 4,678,268 A | 7/1987 | Russo et al. |
| 4,713,347 A | 12/1987 | Mitchell et al. |
| 4,714,345 A | 12/1987 | Schrader |
| 4,775,515 A | 10/1988 | Cottingham |
| 4,780,423 A | 10/1988 | Bluestein et al. |
| 4,912,051 A | 3/1990 | Zaromb |
| 4,963,498 A | 10/1990 | Hillman et al. |
| 5,120,643 A | 6/1992 | Ching et al. |
| 5,183,740 A | 2/1993 | Ligler et al. |
| 5,372,783 A | 12/1994 | Lackie |
| 5,554,340 A | 9/1996 | Lackie |

FOREIGN PATENT DOCUMENTS

| | | |
|---|---|---|
| EP | 0206077 | 6/1986 |
| EP | 0317286 | 11/1988 |
| EP | 0404258 | 6/1989 |
| GB | 2 190 490 | 11/1987 |
| WO | WO 80/02747 | 12/1980 |
| WO | WO 89/06799 | 7/1989 |
| WO | WO 90/07380 | 7/1990 |
| WO | WO 93/14403 | 7/1993 |
| WO | WO 94/03104 | 2/1994 |

OTHER PUBLICATIONS

Jolley et al., "Particle concentration fluorescence immunoassay (PCFIA): a new, rapid immunoassay technique with high sensitivity", : 21.

Sato et al., "A novel method for isolating specific endocytic vesicles using very fine ferrite particles coated with biological ligands and the high–gradient magnetic separation technique", J. Biochem., 100: 1481, Dec. 1986.

Goldberg et al. "Methods for measurement of antibody/antigen affinity based on ELISA and RIA", *Curr. Op. Immunol.* 3:278, 1993.

Dill et al., "Antibody–Antigen Binding Constancts Determined in Solution–Phase with the Threshold Membrane–Capture System: Binding Constants for Anti–Fluorescein, Anti–Saxitoxin, and Anti–Ricin Antibodies", *Anal. Biochem.* 217:128, 1994.

(List continued on next page.)

*Primary Examiner*—Bao-Thuy L. Nguyen
(74) *Attorney, Agent, or Firm*—Choate, Hall & Stewart; Brenda Herschbach Jarrell

(57) ABSTRACT

The present invention provides an improved system for detecting the presence or level of an analyte in a sample. In "competition-like" assays of the present invention, a sample including an analyte is mixed with a second ligand to which the analyte binds, and the mixture is exposed to a solid phase containing a first ligand that can compete with the analyte for binding to the second ligand. According to the present invention, the time of exposure of the mixture to the solid phase is limited so that substantially no dissociation of analyte/second ligand complex occurs. The competition-like assays of the present invention are preferably performed with a solid phase containing a substantial excess of first ligand. In "sandwich-type" assays of the present invention, a sample including an analyte is contacted with a solid phase including a first ligand that binds the analyte and, simultaneously or subsequently, is contacted with a second ligand that binds the analyte (or the analyte/first ligand complex). The time of contact between the second ligand and the solid phase is limited so that substantially no non-specific binding between the second ligand and the solid phase occurs.

24 Claims, 12 Drawing Sheets

OTHER PUBLICATIONS

Freytag et al., "Affinity–column–mediated immunoenzymometric Assays: Influence of Affinity–Column Ligand adn Valency of Antibody–Enzyme Conjugates", Clin. Chem. 30/9, p. 1494–1498, 1984.

Friguet et al., "Measurements of the true affinity constant in solution of antigen–antibody complexes by enzyme–linked immunosorbent assay", Jour. of Immun. Methods, 77, p. 305–319, 1985.

Pollema et al., "Sequential injection immunoassay utilizing immunomagnetic beads", Anal. Chem. 64, p. 1356–1361, 1992.

Gunaratna et al., "Noncompetitive flow injection immunoassay for a hapten, α–(Difluoromethyl)ornithine", Anal. Chem, 1993, 65, p. 1152–1157.

G. Gübitz et al., "Flow–injection immunassays", Analytica Chimica Acta, 283, 1993, p. 421–428.

Pollema et al., "Flow injection renewable surface immunoassay: a new approach to immunoanalysis with fluorescence detection", Anal. Chem., 1994, p. 1825–1831.

Forrest et al., "Liposome Enhanced Flow Injection Immunoanalysis", Biotechnology, V. 14, p. 1–11, 1988.

Freytag et al., "A Highly Sensitive Affinity–Column–Mediated Immunometric Assay, as Exemplified by Digoxin", Clin. Chem. 30/3, 417–420, 1984.

Freytag et al., "Affinity–Column–Mediated Immunoenzymometric Assays: Influence of Affinity–Column Ligand and Valency of Antibody–Enzyme Conjugates", Clin. Chem. 30/9, 1949–1498, 1984.

Glaser et al., "Antigen–Antibody Binding and Mass Transport by Convection and Diffusion to a Surface: A Two–Dimensional Computer Model of Binding and Dissociation Kinetics", Anal. Biochem, V. 213, 152–161, 1993.

Hudson, "Infrared Systems Engineering", Wiley–Interscience, 1969.

O'Shannessy et al., "Determination of Rate and Equilibrium Binding Constants for Macromolecular Interactions Using Surface Plasmon Resonance: Use of Nonlinear Least Squares Analysis Methods", Anal. Biochem., V. 212, 457–468, 1993.

Perseptive Biosystems, "ID™ Real–Time Immunoassay", Product Report, and prec. 1st, Jul. 1992.

Plant et al., "Liposome Enhanced Flow Injection Immunoanalysis", Biotechnology, vol. 6, Mar. 1988.

Pollema et al., "Sequential Injection Immunoassay Utilizing Immunomagnetic Beads", Anal. Chem. 64, 1356–1361, 1992.

Sambucetti et al., "Process for Purification of Magnetic Ink", IBM Technical Disclose Bulletin, vol. 18, No. 2, p. 593–595, Jul. 1975.

Smith, "Modern Optical Engineering. The Design of Optical Systems", McGraw–Hill Inc. (pubs) ©1966.

Warden et al., "Repetitive Hit–and–Run Fluoroimmunoassay for T–2 Toxin", Analytical Biochemistry 162, 363–369, 1987.

PCT Search Report, May 30, 1995.

Ekins et al., "Multianalyte Microspot Immunoassay–Microanalytical "Compact Disk" of the Future", Clin. Chem. 37/11, p. 1955–1967, 1991.

Friguet et al., "Measurements of the True Affinity Constant in Solution of Antigen–Antibody Complexes by Enzyme–Linked Immunosorbent Assay", Jour. of Immunological Methods, vol. 77, p. 305–319, 1985.

Skubitz et al. "Determination of Antibody–Hapten Association Kinetics: A Simplified Experimental Approach", Jour. of Immunology, vol. 114, No. 4, Apr. 1975.

SOLID PHASE ASSAY FOR DETECTION OF LIGANDS

This application is a continuation-in-part of commonly owned U.S. patent application Ser. No. 08/262,741, filed on Jun. 20, 1994 now abandoned, which is a continuation of U.S. patent application Ser. No. 08/197,431, now abandoned, filed on Feb. 16, 1994, which is a continuation-in-part of 07/924,720, filed on Aug. 3, 1992, now U.S. Pat. No. 5,372,783. The entire contents of each of these parent applications are hereby incorporated by reference.

FIELD OF THE INVENTION

The invention relates to chemical, biochemical, and biological assays, and more particularly to solid phase assays for the detection of ligands.

BACKGROUND OF THE INVENTION

Assays in which a sample and one or more reagents are variously reacted to form a ligand/conjugate complex such as an antibody/antigen or similar complex, which may then be observed in order to measure the presence or level of a predetermined moiety in the sample, are well known. Typically, an antibody is used to assay for the presence of an antigen for which the antibody is specific. These assays have been extended to quantitate haptens such as hormones, alkaloids, steroids, antigens, antibodies, nucleic acids, and fragments thereof, enzymes, and cell surface receptors. It is in this broad sense that the term "ligand/conjugate" as used herein should be understood.

Sensitive immunoassays typically use tracer techniques in which a tagged constituent of the complex is incorporated, for example in the reagent, the non-complexed tagged reagent then being separated from the complexed reagent. Thereafter, the complex can be quantitated by observing a signal from the tag. Radioisotopes, fluorescent and chemiluminescent molecules, calorimetric tags, and other markers have been used to label constituents or moieties of the complex, appropriate apparatus being employed to detect and measure the radiation from the label.

In such assays where at least one component of the complex is initially bound to a solid substrate preparatory to formation of the complex, a basic problem arises because of the typically lengthy time required to bind that component to the solid substrate such as a well microtiter plate or bead, sometimes requiring incubation times on the order of hours for binding of a component to the solid phase to occur notwithstanding such expedients as heating, agitation and the like. Consequently, there is a significant amount of prior art regarding attempts to reduce this incubation time, including using microbeads, dipsticks, macrobeads, etc., but nonetheless incubation times on the order of 10 to 20 minutes are typical.

There are numerous formats for solid phase assays, but they can nonetheless be sorted into two types: sandwich and competition, both of which are well known to those skilled in the art. Sandwich assays typically require the antigen to be able to simultaneously bind to more than one conjugate. One of the conjugates is attached to the solid phase while the other conjugate is labeled with a tag. The amount of tagged conjugate attached to the solid phase is then related to the antigen concentration in a sample. A universal problem in sandwich assays is nonspecific binding, i.e., the amount of labeled conjugate that is on the solid phase, but not attached to the antigen. In designing sandwich assays, there is usually a trade-off between signal level and nonspecific binding. Increasing the concentration of labeled conjugate or incubation time of the labeled conjugate will increase the signal levels, but will also increase the amount of nonspecific binding.

Various approaches have been used to try to reduce the effect of nonspecific binding including wash buffers, detergents, blocking steps, referencing, etc., which are also well known in the art.

In competition assays a labeled moiety, either a conjugate to or an analog of the antigen, can be bound to the solid phase. The presence of antigen reduces or inhibits the binding of the labeled moiety to the solid phase. The amount of inhibition in the signal is a measure of the antigen concentration. For a competition assay to work well the amount of antigen, labeled moiety and solid phase binding sites must be roughly equal. Therefore, competition assays are usually much less sensitive than sandwich assays and also suffer from a small linear range. They are nonetheless useful for small antigens which can only bind with one conjugate at a time.

The results of chemical, biochemical, and biological assays are used to make important decisions, and therefore, the accuracy and reliability of the result is of utmost importance. Heretofore, control samples of known concentration are assayed periodically, or even simultaneously with the sample to be measured, to calibrate and verify the operation of the assay on the unknown sample. This process reduces, but does not eliminate, the possibility of error in the assay of interest.

An object of the present invention is to provide a solid phase assay method which solves many of the problems described above. Another object of the invention is to provide a "competition-like" assay with an increased linear range of determination, improved sensitivity, reduced susceptibility to errors caused by deteriorating reagents or variations in environmental conditions, reduced susceptibility to errors caused by bubbles or other mechanical problems, ease of automation, and reduced time to obtain a final result of the assay, among other things, relative to standard competition assays known in the art. A "competition-like" assay of the invention is similar to a standard competition assay except that at least one step of the competition-like assay of the invention is time limited in a manner described herein so that competitive equilibria typical of standard competition assays are not established.

Another object of the invention is to provide an improved sandwich assay in which at least one step is time limited so that problems that are associated with non-specific binding reactions and are typical of standard sandwich assays are avoided.

Yet another object of the invention is to eliminate time-consuming incubation steps in a solid phase assay method or to significantly reduce the required time to run the assay.

SUMMARY OF THE INVENTION

The above objects are accomplished by the present invention which comprises a method of performing binding assays, utilizing a solid phase, in which at least one or more of the analyte and/or ligand components is or are allowed only a limited contact time with the solid phase component. In the present methods, the solid phase material is preferably coated with a substantial excess of binding ligand. In the preferred embodiments, as described in our co-pending, commonly assigned U.S. patent application Ser. No. 07/924,720, the contact time of the solid phase component with the analyte-containing sample of the reagent-containing sample is limited by means of flowing the sample relatively rapidly past the solid phase material. The present invention comprises several variations and improvements, described in more detail below, each of which includes the limited solid phase contact time.

The present invention comprises methods of detecting the presence or level of an analyte in a sample by detecting the formation of a binding complex on a solid phase. Preferred "competition-like" methods of the invention comprise the steps of:

(a) mixing the sample with a second ligand capable of binding with said analyte so that an analyte/second ligand complex is formed;

(b) contacting the mixture produced in step (a) with a solid phase having bound thereto a first ligand capable of binding with the second ligand so that a first ligand/second ligand complex is formed, the contacting being performed under conditions and for a time sufficiently limited that dissociation of the analyte/second ligand complex formed in step (a) is substantially inhibited;

(c) binding a detectable tag to the second ligand-either prior to or after step (a) or step (b) so that a portion of the tag is retained on the solid phase upon formation of the first ligand/second ligand complex;

(d) detecting the portion of the tag to detect formation of the first ligand/second ligand complex on the solid phase, so that the presence or level of the analyte in the sample can be determined.

As will be readily appreciated by one of ordinary skill in the art, such competition-like assays could also be used to quantify the binding constant for a particular binding ligand such as, for example, an antibody.

Preferred "sandwich-type" methods of the invention comprise the steps of:

(a) contacting the sample with:
(i) a solid phase having bound thereto a first ligand capable of binding the analyte; and
(ii) a second ligand capable of binding to the first ligand or to a first ligand/analyte complex so that a first ligand/analyte/second ligand complex is formed on the solid phase, the contacting being performed under conditions and for a time sufficiently limited that any non-specific binding between the second ligand and the solid phase is substantially inhibited;

(b) binding a detectable tag to the second ligand either prior to or after formation of the first ligand/analyte/second ligand complex so that a portion of the tag is retained on the solid phase upon formation of the first ligand/analyte/second ligand complex;

(c) detecting the tag to determine the presence or level of the analyte in the sample.

The invention also provides methods for single-point calibration and quality assurance that can be used in conjunction with the above-mentioned competition-like and/or sandwich-type assays.

The present invention involves substantially increasing the sensitivity of standard competition-type and sandwich-type immunoassays by a process wherein at least one or more of the analyte and/or ligand components is flowed over the surface of and contacts a solid phase device (e.g. beads, a capillary tube interior surface, a microtiter plate or other device), the solid surface having been suitably coated or impregnated in advance with a binding partner of the analyte and/or ligand.

As described hereinafter, in some cases the analyte-containing fluid is pre-reacted with a label or a labelled binding partner for the analyte. In other instances, after the analyte-containing sample is flowed over and contacts the solid surface, at least one additional solution containing a tagged second binding partner, a tagging agent or a tag component is also flowed over and contacts the solid surface. The solid surface may then be washed with a suitable washing solution and the signal intensity of the tag immediately measured.

Alternately, as in the preferred embodiment described in the following paragraph, the accumulation of label on the solid phase material may be monitored continuously in real time. In this case, in at least some assays, the wash step is unnecessary as the rate of accumulation of signal may be successfully used to accurately quantify analyte.

In the preferred embodiment, the assays of this invention may be conducted in a system comprising the flow cell system described in co-pending U.S. patent application Ser. No. 07/924,720. In preferred embodiments of the system, at least one separate mass of discrete beads coated with a binding partner, is disposed within a cylindrical capillary conduit, which is preferably transparent and is arranged within and passes through the focal region of a focusing lens means. The cylindrical conduit is positioned transversely to the optical axis of the lens means and behind the center of curvature of the lens means. As already noted, the assays of this invention can also be conducted in various other systems, typically with lower sensitivity as hereinafter described, including immunologically coated capillaries, microtiter plates, etc.

In this system, when the coated mass of beads or the like is translucent and the capillary is translucent or transparent, the development of fluorescence can be monitored and measured as the assay proceeds, using optical measuring equipment and an electrical detector means as proposed in U.S. patent application Ser. No. 07/924,720. Measurement of tagged ligand/conjugate complexes bound to other solid surfaces can be made, depending upon the nature of the tag, using measuring means heretofore utilized in such measurements.

The assays of this invention, in general, contemplate coating the solid surface with a substantial excess of a binding partner (for sandwich assays) or analog (for competition-like assays) of the analyte, flowing the analyte-containing fluid and/or any other fluids over and in contact with the solid surface at a rapid rate and under conditions which expose the surface area of the solid to the analyte- or other reactant-containing fluid to the maximum possible extent.

It is believed that a key element of the invention is that the contact time of the analyte and reagent containing solutions and the solid phase material be relatively short. For example, in the preferred embodiment, only a relatively small volume of the analyte (about 2 microliters) is in contact with the solid phase material at any given time.

For competition-like assays of the present invention, "contact time" refers to the average amount of time that an individual analyte/second ligand complex is in contact with the solid phase. At typical flow rates, each "increment" of pre-mixed sample (where "increment" refers to a volume containing, on average, a single analyte/second ligand complex) is in contact with the solid phase for less than about one minute, preferably less than about ten seconds, and most preferably less than about one second. For example, at a flow rate of 1000 ul/min, each increment of pre-mixed sample is typically in contact with the solid phase for only approximately one five-hundredth of a minute.

For improved sandwich assays of the present invention, "contact time" refers to the total amount of time that second ligand is in contact with the solid phase.

While the optimum contact time may vary with other assay parameters including the binding kinetics of the particular analyte being studied, it is anticipated that the optimum contact time in all cases will be relatively short.

The assays of this invention are applicable to a wide range of analytes including monovalent and polyvalent entities. These assays can be directly conducted successfully on suitably diluted samples of fluids heretofore considered difficult to assay directly, such as, e.g., whole blood, milk, etc.

The assay methodology of this invention has numerous advantages over the methodology conventionally used in the art. These advantages include, but are by no means limited to, faster running time, greater sensitivity especially at low analyte concentrations, elimination in many cases of incubation time and diminution thereof in all cases, ease of automation, and high reproducibility, and in the particular case of competition assays, extended linear range.

As described below, using the present assay methodology, one may establish a specific performance curve for each analyte whereby false negatives and false positives due to abnormally high levels of binding and erratic results caused by performance errors can be readily eliminated.

Using the methodology of the present invention, single point calibration with a fluid of known antigen concentration can be utilized for competition-like assays as well as those of the sandwich type. This is particularly useful in eliminating false negatives and false positives due to abnormally low binding levels (e.g., such as may be caused by the presence of inactive antibodies). Other and further advantages and benefits of the present invention are discussed hereinafter or will be apparent from the detailed discussion below.

DETAILED DESCRIPTION OF THE INVENTION

Figure 1:
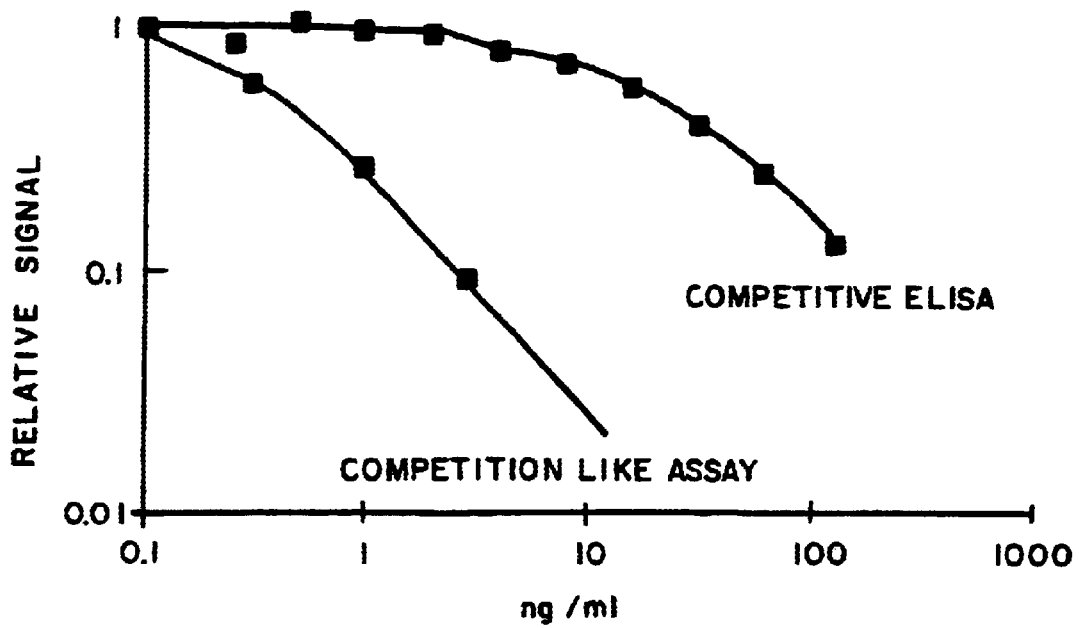
FIG. 1 shows a comparison of the present invention to a standard ELISA assay.

The present invention rests on the finding that competition and sandwich immunoassays can be run, with reproducible and otherwise satisfactory results, within very short time spans, by a process that comprises the step of rapidly flowing a sample containing analyte over and in contact with a solid surface that has been impregnated or coated with a substantial excess of, for example, an immunological binding partner for the analyte.

The presence of a label, while essential, can be effected in a variety of ways. Thus, the diluted analyte sample may be pre-reacted with labeled antibody or the labeled antibody solution may be flowed over and in contact with the solid surface immediately after flowing the analyte thereover. The label may be directly bound to a primary antibody for the analyte or it may be bound to a secondary antibody which is then either (a) pre-reacted with primary antibody and analyte, (b) pre-reacted with primary antibody whereupon the product is then rapidly flowed over and in contact with the solid substrate, to at least some of the active sites of which analyte has already been bound, (c) flowed rapidly over and in contact with the solid substrate, to at least some active sites of which an analyte-primary antibody conjugate has already been bound.

It has been found that in working with samples of analytes of known concentration, different binding curves will be obtained depending upon whether some or all of the immunoreactants are pre-reacted prior to flowing the solution containing the analyte over the solid surface to which its immunological binding partner is coupled. If, however, the binding curve is carefully established based on runs made with analyte samples of known concentration using identical reagents and method steps in each run, it can be successfully utilized with analyte samples of unknown concentration to give results that are highly reproducible and precise.

Stated otherwise, the immunoreactants, including the labeled primary or secondary antibody, must be mixed with the diluted analyte sample in the same order for the same time periods and contacted with the immunologically treated solid surface in the same order at the same flow rates and under the same conditions of contact as well as other conditions that may have an effect such as, e.g., agitation (or lack thereof) and temperature. The maintenance of identical methodology becomes increasingly critical as the time of exposure of the analyte to its solid-bound immunological binding partner is decreased.

In conducting competition-like immunoassays in accordance with this invention, the contact time between any given analyte molecule, or any given analyte/second ligand complex, and the solid surface to which its immunological binding partner is coupled is very small. To date, in the experimental evaluation of the assay method of this invention, solutions containing analyte have been flowed over and in contact with a solid substrate, to which an immunological binding partner of the analyte is coupled, in a cylindrical column (approximately 1.7 mm in diameter), at flow rates that have varied between 250 and 2000 microliters per minute. While slower and faster flow rates may well work under certain circumstances, it is presently believed that this range is optimal for insuring the requisite contact between the analyte and its binding partner immobilized on the solid surface while assuring a relatively short contact time, as described above.

Using the stated range of flow rates for analyte-containing solution, competition-like immunoassays according to this invention have so far been conducted under circumstances where the solid substrate is continuously contacted with sequential incremental volumes of analyte for a period of from about one to about two minutes. This time is believed to be of less importance to competition-like assays of the invention than the contact time between any single volume increment of analyte and the solid phase material (though, as discussed herein, the situation is different for sandwich assays of the invention). In all competition-like assays investigated so far, the contact time between any single volume increment of analyte and the solid phase material has been less than about one minute, preferably less than about 10 seconds, and most preferably less than about one second.

While it is contemplated that, depending upon the nature of the analyte and its immobilized binding partner, the configuration and arrangement of the solid substrate, the reaction temperature and perhaps other variables as well, contact times of the analyte solution with its immobilized binding partner ranging between about 25 seconds and 5 minutes (i.e., 300 seconds) may in some instances be desirable, it is believed that the time range so far utilized of 60–120 seconds (i.e., 1–2 minutes) is particularly effective when the solid substrate exhibits a high surface area—as, e.g., when it comprises a mass of beads, each of about 100 microns in mean diameter.

It is contemplated that the methodology of the invention is usable with a wide variety of solid substrates and is by no means limited to use with beads. It is noted that preferred solid substrates as alternatives to beads, e.g., synthetic polymer masses suitable as substrates for immunogens are available in the form of foamed and filamentous structures, as loosely woven mat-like structures and in a variety of other forms in addition to beads. Moreover, as is well-known in the art, glass or plastic tubes and other devices coated with immunological reactants are suitable as solid substrates. In the method of the present invention, it is contemplated that capillary tubes with appropriate interior immunological coating and coated microtiter plates, for example, could readily afford the requisite contact with analyte-containing sample during rapid flow.

It is further believed that other devices such as cassettes, microfilters and the like can readily be adapted to serve as chambers within which the rapid flow, contact reaction between analyte in solution and solid-coupled immobilized binding partner can advantageously be carried out.

A reaction chamber which has been found to function efficiently in the present invention is the capillary conduit that passes through the lens means described in copending U.S. patent application Ser. No. 07/924,720.

The system described in the aforementioned copending application is disclosed to be particularly adapted to the use of fluorescent tags and to optical detection of the fluorescence as it develops throughout an assay. The present invention contemplates that the tags employed can be of the fluorescent, luminescent, or calorimetric type; indeed, the well-known radioactive tags, which are not preferred for environmental and health reasons, are also useful. Indeed, any tag that will produce a detectable signal, preferably by electrical or electronic means can be utilized.

In this regard, it is noted that the aforementioned co-pending patent application Ser. No. 07/924,720 employs an optical detection system that conveys a signal to an electrical detector. According to the co-pending application, the total fluorescence is optically detected continuously as the immunoassay reaction proceeds.

It should be noted that the monitoring of total fluorescence throughout an immunoassay is not necessarily the same as monitoring immunological binding of analyte to immobilized binding partner. At certain stages of the assay, total fluorescence developed will greatly exceed fluorescence attributable to immunologic binding for various reasons, including the presence of unbound tagged primary or secondary antibody, the occurrence of nonspecific binding, etc. In addition, the electrical signal, which includes that from the total optically detected fluorescence, does not separate the latter from its own system noise or from baseline scattering of fluorescence that may be detected when no analyte is present.

Despite these caveats, it has been found that monitoring the total fluorescent signal developed during an assay, and in particular monitoring the rate of accumulation of signal during an assay, yields a highly satisfactory (in terms of sensitivity, reproducibility etc.) measure of analyte concentration, e.g. see Examples 5 and 6 below. This ability to monitor signal in real time is also critical for implementation of the quality assurance invention described below.

A single point calibrator form of assay can be successfully utilized to perform both sandwich and competition type assays of the present invention. Use of the single point calibrator assay has particular appeal, e.g., in reference laboratories. Among the known advantages of single point calibrator assays is that they avoid the need to conduct separate assays on reference standard samples essentially contemporaneously with the assay of samples of unknown analyte concentration; they afford a direct indication with the same solid substrate of the comparative reference standard/unknown sample binding in the assay. As is also known, if the immobilized binding partner on the solid substrate is, e.g., partly inactive for some reason, the single point calibrator result is valid nonetheless because it is performed on the same solid substrate and with the same reagents with samples of both known and unknown concentration.

As indicated, the assays of this invention can readily be automated in whole or in part. They can be designed to be run in a defined apparatus under circumstances wherein the assay reactants, including the solid substrate impregnated with the immunological binding partner of the desired analyte, the tag or tagged antibody, the buffer and analyte reference standards are packaged in kit form. Such kits may include, e.g., disposable reaction chamber devices such as cassettes, receptacles for beads, coated capillaries, etc.

Ability to monitor the signal in real time has the additional advantage of permitting the establishment of "quality assurance" curves for the assays of given analytes with specified reagents and process sequences. Construction of quality assurance curves is effected by:

(1) Fitting raw output data to a mathematical function. This will depend in part upon the data parameters selected to be utilized and in part upon the process sequence, since a mathematical function for a given assay may consist of several functions, each covering a specified time interval of the assay. Once the function is established, a standard fitting algorithm (such as that for least squares regression) is used to vary the function parameters and achieve a statistical "best fit" curve. The algorithm will be utilized so as to minimize "residual error" where the latter is defined as the difference between the fitted function and the existing data.

(2) Comparing each residual error with a pre-programmed threshold value. A computer can perform this task.

(3) Thereafter using the computer to flag runs wherein the residual error exceeds the threshold value and depending upon the extent of assay automation, to either cause the assay to be automatically rerun or to discard it as flawed.

The threshold values will be determined by fitting the function to accumulate sets of both good and bad data and will be subject to reevaluation as further data is collected.

By fitting, insofar as is feasible, to equations based on binding kinetics, the use of quality assurance may enable rejection of false positives and of false negatives due to abnormally high nonspecific binding. In any event, it will reject values due to assay process malfunction, e.g., such as that caused by air bubbles, discussed in some of the Examples that follow.

Various kinetic explanations based on known first and second order phenomena have been proposed for the assays of this invention and have met with considerable success in describing the outcome of various experiments. Nevertheless, these explanations are regarded as tentative and are included here purely as an aid to understanding and are in no way to be interpreted as limiting the scope of the invention, as set forth in the claims below.

In one embodiment of the present invention, we perform a competition-like assay in which we pre-react the sample containing analyte with an analyte-specific antibody and then flow the pre-reacted mixture past the solid phase, which is also capable of binding the analyte-specific antibody.

A tentative explanation for the excellent results we obtain is that the relatively brief (much less than a second) time of contact of each increment of volume of the pre-reacted mixture with the solid phase substantially inhibits the establishment of a classical three-way competitive equilibrium, as occurs if pre-formed analyte/antibody complexes are dissociating while antibody/solid phase complexes are forming. Instead, we hypothesize that the observed signal is due almost entirely to the binding of the residual free (i.e. not complexed to sample antigen) antibody left in the pre-reacted mixture. This effect is thought to arise because of the relatively slow rate of dissociation of analyte/antibody complex. In essence, very few of the complexed antibody/antigen pairs will dissociate during the short contact time.

As a test of this theory, we fit it to two sets of data. One set of data was obtained using a prototype immunoassay system, as described in copending application Ser. No. 07/924,270. The other set of data was obtained using standard ELISA technology.

The following Examples are presented as illustrative of the invention rather than limiting.

In the assays presented in the Examples, the emission from the fluorescent indicator tags was optically directed in accordance with the disclosure of the aforementioned copending application to an electrical detector comprising a computer programmed to calculate each of (1) "delta" defined as the difference between the detected baseline and the detected endpoint, (2) the slope of the signal accumulation, as monitored in real time, (3) "sigma", the standard deviation among multiple identical sample runs, and (4) "C.V.", the coefficient of variation of these identical runs.

The invention further comprises means for performing a "quality assurance" analysis of the assay either during performance of the assay or at a later time. The analysis provides a determination of whether some of the assay results should be rejected due to errors or deficiencies.

The invention further comprises a calibration liquid which can be used to check the performance of the assay solid phase material and other associated analytical ligands within a few seconds of the time that these materials are used to assay an unknown sample. While use of a calibrator of this sort is well known in sandwich immunoassay art, its use with a competition assay format has never been accomplished or disclosed.

In the preferred embodiment, the solid phase consists of a fluid permeable porous mass which typically has a substantial excess of a first binding ligand immobilized on its surface. This porous mass may consist of a multitude of particles contained in a flow cell and held in place by a support means such as a fluid permeable screen. The screen may either be fixed permanently in the flow cell, or may be formed temporarily as described in U.S. patent application Ser. No. 08/026,507, also incorporated in its entirety by reference herein.

In accordance with the present invention the analyte containing sample will be brought into intimate contact with the solid phase material for a relatively short period of time. In the preferred embodiment of the competition-like assay of the present invention, the sample will be flowed through the porous mass of the solid phase material. In this case, the contact time is understood to refer to the time during which each increment of volume is in contact with the solid phase.

It will be appreciated that a label or tag is necessary in order to detect the amount of second binding ligand immobilized on the solid phase. Any radiation emitting tag can be used with the present invention, including, but not limited to, fluorescent tags, chemiluminescent tags, bioluminescent tags, radioisotope tags, calorimetric tags, etc. It will be further appreciated that the label or tag may be coupled directly to one of the primary binding ligands utilized in the assay, or may be coupled to the primary binding ligand through an intermediary third binding ligand capable of forming complex with the appropriate primary binding ligand. Techniques utilizing an intermediary third binding ligand are, in the specific case of antibody-based assays, typically referred to as "second antibody techniques" by those skilled in the art.

Preferably, a competition-like assay of the present invention is performed in the following steps: A substantial excess of a first binding ligand, typically either the sample analyte or an analog of the sample analyte, is bound to the porous solid phase material. The sample, containing an unknown quantity of analyte, is mixed with a typically limiting quantity of labeled second binding ligand. The mix of second binding ligand and sample is then flowed past the solid phase material.

As is known in the art, standard competition assays are typically utilized to determine the presence or amount of an analyte in a sample. This determination typically involves a comparison of the level of first binding ligand/second binding ligand complex formation (typically assayed by detecting the presence and/or amount of a second-binding-ligand-associated detectable tag that is retained on the solid phase) that is achieved in the absence of analyte, with the level of first binding ligand/second binding ligand complex formation that is achieved in the presence of a sample that contains an unknown amount of analyte (for example, when the sample and second binding ligand have been pre-reacted; or when the sample, first binding ligand, and second binding ligand are all reacted simultaneously).

The competition-like assays of the present invention can be utilized in the same way. For such assays, it is important that formation of analyte/second binding ligand complexes inhibits formation of first binding ligand/second binding ligand complexes.

The mixing of second binding ligand and sample analyte may be performed prior to introduction of the mixture to the flow system, or it may be accomplished automatically, e.g. by injecting a stream containing second binding ligand into a flowing stream of analyte containing sample.

It is an object of the present invention to enable quantitation of the sample analyte using a substantial excess of first binding ligand on the solid phase by limiting the contact time of the premixed sample and labeled second binding ligand with the first binding ligand on the solid phase. This will be understood by those skilled in the art to represent a departure from previously understood practice in which the concentration of solid phase binding ligand must be roughly equal to the concentration of analyte to be detected.

Preferably, a single point calibration can be performed in the case of the competition-like format by incorporating the following steps: Either immediately before, or immediately after performing a competition-like assay as described above, a known reference liquid, typically a known concentration of analyte compound or analog thereof is mixed with another aliquot of labeled second binding ligand drawn from the same source as that used with the sample analyte. After combining, which may be accomplished automatically as described above, the mixture of reference liquid and labeled second binding ligand is again brought into intimate but temporary contact with the solid phase. Two signals are measured, one arising from the reference liquid and one arising from the sample. Since the reference liquid is of known properties, the signal arising from it can be used as a reference to compensate for variations in labeled second binding ligand activity, first binding ligand activity, and the like. It will be appreciated that this single point calibration is enabled by the excess solid phase binding capacity, effective utilization of which is a primary object of the present invention.

Preferably, a sandwich assay of the present invention is performed in the following steps: A substantial excess of a first binding ligand, capable of binding the analyte of interest, is immobilized on the solid phase material. The sample is brought into intimate but temporary contact with the solid phase material, as by flowing. A second labeled binding ligand, capable of forming a complex with the sample analyte/first binding ligand complex is then brought into intimate but temporary contact with the solid phase material, again, as by flowing. The amount of analyte is then quantified by measuring the amount of labeled binding ligand retained on the solid phase material. Those skilled in the art will appreciate that the referred to quantitation of analyte will require subtraction of a non-specific binding (i.e. binding of the labeled second ligand in the absence of analyte) term which is always found to be present in sandwich assays. It is an object of the present invention to increase the ratio of specific binding over non-specific binding by limiting the contact time between the labeled second binding ligand and the solid phase material.

Preferably, a quality assurance method can be implemented on either the competition-like assay or the sandwich assay of the present invention by monitoring and recording, typically on a computer, the course of the signal generation during the assay. By comparing the shape of the resultant signal curve versus time to a pre-determined standard curve, errors due to air bubbles, other mechanical problems, and the like will be readily detectable.

An important element of the invention is that the contact time of the analyte and/or reagent containing solutions with the solid phase material be relatively short. For example, in a preferred embodiment utilizing the capillary flow cell and porous solid phase, as described fully in copending U.S. patent application Ser. No. 07/924,720, only a relatively small volume of the analyte (about 2 microliters) is in contact with the solid phase material at any given time.

Typical competition-like assays of the present invention were performed at flow rates of approximately 1000 ul/min. For such assays, each increment of analyte is in contact with the solid phase for an average of only approximately one five-hundredth of a minute, or slightly over a tenth of a second. While the optimum contact time has not yet been precisely determined, and while it is believed that the optimum time will vary with other assay parameters including the binding kinetics of the particular analyte being studied, it is certainly anticipated that the optimum contact time in all cases will be relatively short.

By "relatively short" or "relatively brief" as used herein, it is meant that contact time of the sample and reagent containing solutions with the solid phase, depending on the binding kinetics of the analyte, will be less than about one minute, preferably less than about ten seconds and most preferably less than about 1 second.

In various assays, flow rates ranging from about 250 ul/min to about 2000 ul/min have been investigated. Flow rates in this range have been found to be suitable for a wide variety of analysis and sample matrices, but the invention is in no way limited to this range of flow rates.

Relatively simple models based on first order binding kinetics have been proposed and have met with considerable success in describing the outcome of various experiments. These models, and explanations based on them, are regarded as tentative and are included here purely as an aid to understanding and are in no way to be interpreted as limiting the scope of the invention, as set forth in the claims below.

In one embodiment of the present invention, we perform a competition-like assay in which we pre-react the sample that contains an unknown amount of analyte with a specific antibody and then flow the pre-reacted mixture past the solid phase, which has a substantial excess of the analyte material immobilized on it and is thus also capable of binding the specific antibody. In a competition-like assay the important parameter is the mean contact time of any portion of the sample with the solid phase, not the contact time of the solid phase with the total sample.

While not wishing to be bound by any particular theory, it is believed that a tentative explanation for the excellent (e.g. highly sensitive, highly reproducible, exhibiting a large linear range) results we obtain is that the relatively brief (less than a second) time of contact of each increment of volume of the pre-reacted mixture with the solid phase essentially prohibits the establishment of a classical three way competitive equilibria. Instead we hypothesize that the observed signal is due almost entirely to the binding of the residual free (i.e. not complexed to sample antigen) antibody left in the pre-reacted mixture. This effect is thought to arise because of the relatively slow rate of dissociation of antibody-antigen complex. In essence, very few of the complexed antibody antigen pairs will dissociate during the short contact time. In other words, by limiting contact time between the solid phase and increments of pre-reacted mixture, we are able to avoid the problems associated with competing reactions.

As a test of this theory, we used two assay methods, one described in copending U.S. patent application Ser. No. 07/924,720, and one using standard ELISA technique and plate readers. In both cases the coating of the solid phase material was as nearly identical as possible to facilitate comparison. Equations were derived to approximate both the model described above and a standard three way competitive equilibria. The equations used to approximate the "competitive like" model assumed that the labeled antibody reached equilibrium with the antigen in the sample, and that the residual free antibody then reached equilibrium with the solid phase. This model is thought to be a gross simplification of the actual process and is in no way intended to limit the scope of the Invention. Unknown parameters in this assay were the antibody affinity and the effective concentration of the solid phase antigen. As shown in FIG. 1, reasonable values (antibody affinity=$4\times10^9$ and effective solid phase antigen concentration=$1\times10^{-8}$ molar) were found for these parameters which still allowed the models to simultaneously fit the two sets of data.

Figure 12:
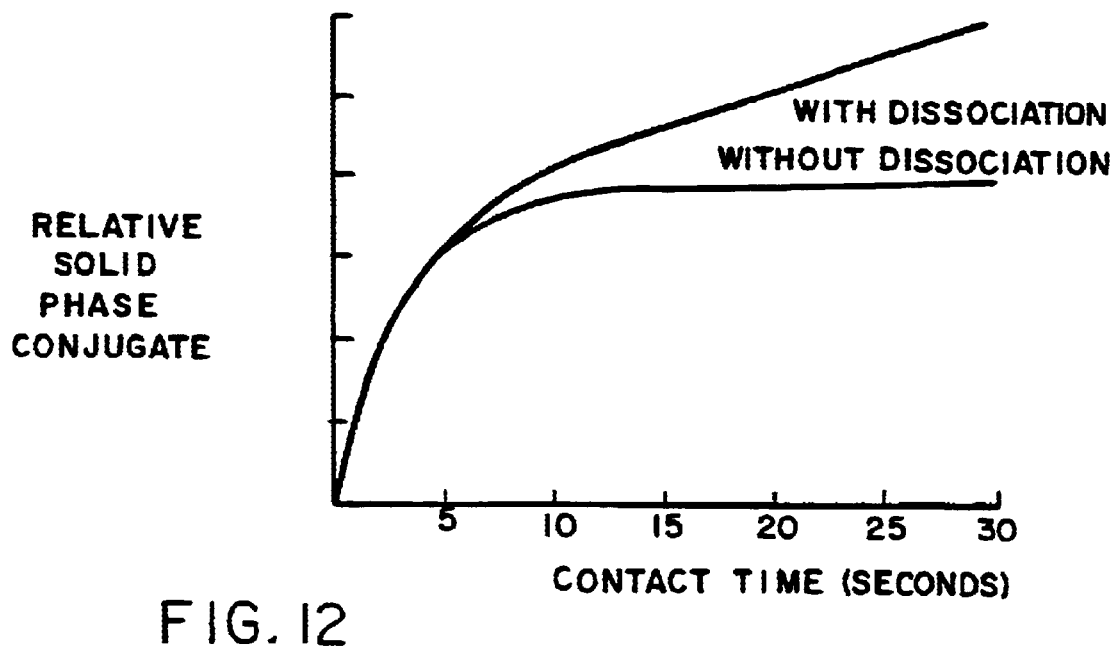
FIG. 12 shows a plot of complex-formation versus time for a typical competition-like assay ("with dissociation"), as compared to an idealized competition-like assay in which there is no dissociation of pre-formed analyte-second binding ligand complexes ("without dissociation").

An alternate way to present this theory is embodied in the graph presented as FIG. 12. FIG. 12 shows a plot of complex formation versus contact time (where "contact time" refers to the time that a single increment of pre-reacted mixture is in contact with the solid phase) for (i) an "idealized" competition-like assay in which there is no dissociation of pre-formed analyte-second binding ligand complexes ("without dissociation"); and (ii) a typical competition-like assay ("with dissociation"). The curves presented in FIG. 12 were calculated using standard mathematical modelling techniques (see, for example, *Chemical Kinetics and Dynamics*. J. I. Steinfeld et al., Prentiss Hall Press, 1989). One of ordinary skill in the art would readily be able to generate similar curves for any binding reactions of interest.

With reference to FIG. 12, it is clear that, if the contact time of the pre-reacted mixture with the solid phase is less than about 5 seconds (for the particular association rate constant shown), then the actual signal observed is virtually identical to the hypothetical case of no dissociation. In preferred competition-like assays of the invention, therefore, the step of contacting the pre-reacted mixture (containing sample and second binding ligand) with the solid phase is performed under conditions and for a time that is sufficiently limited that the binding reaction between the first binding ligand on the solid phase and the second binding ligand has not progressed to a point that a plot of complex formation versus time (such as that presented in FIG. 12, "with dissociation" curve) has diverged substantially from an idealized plot of the same parameters that is generated assuming that no dissociation of the preformed analyte/second binding ligand complex occurs.

The binding of a relatively low concentration of free antibody to a substantially excessive solid phase antigen is an inherently linear process over a fairly large range of free antibody concentrations which is believed to be the cause of the relatively large linear range observed in our examples.

In a preferred embodiment of the single point calibrator, constructed to work in conjunction with the competition-like assay above, we mix a known concentration of antigen (the calibrator liquid) with an aliquot of the labeled antibody drawn from the same location as the labeled antibody mixed with the sample. This mixture is then flowed past the solid phase, typically at the same rate and for the same time as the unknown sample. Using the preferred embodiment of a translucent solid phase deployed in a transparent capillary (see Ser. No. 07/924,720) it is possible to observe the signal generation in real time. In this case, the slope of the signal generation response is found to be a reliable indicator of the analyte concentration. In the case of the single point calibrator we calculate the slope in two regions, one corresponding to the calibrator liquid, the other corresponding to the unknown sample. The slope of the response from the (known) calibrator liquid provides a reference for other possible assay variables, such as antibody activity, temperature, and the like.

Alternatively, the single point calibrator can be implemented using pure labeled antibody. This is similar to using a calibrator liquid with zero antigen but different because there is no dilution of the antibody into the sample or calibrator. Nevertheless, this method can also provide an effective reference.

In the absence of capability to measure signal generation in real time, the calibrator can be implemented by measuring the change in signal level at discrete times, such as before and after passage of the calibrator liquid and before and after passage of the sample antibody mixture.

As described in general terms above, the preferred embodiment of the sandwich immunoassay again utilizes the apparatus described in Ser. No. 07/924,720. The preferred embodiment of the sandwich assay again incorporates the fundamental concept of a limited contact time of labeled reagent with the solid phase. The model here, which again must be regarded as tentative, not limiting, and included for purposes of explanation only, is somewhat different.

As described in the background section above, a common difficulty in implementing high sensitivity sandwich immunoassays is the presence of non-specific binding of the labeled antibody to the solid phase. Although it is not guaranteed to hold for all systems, it is often observed that the non-specific binding signal is slower to reach equilibrium than the specific binding signal. In general terms, we believe that by limiting the contact time of the labeled antibody with the solid phase (i.e. limiting the total time during which labeled antibody is in contact with the solid phase) we are able to effect an increase in the ratio of specific binding over non-specific binding. This effect can be tentatively understood with reference to FIG. 2.

Figure 2:
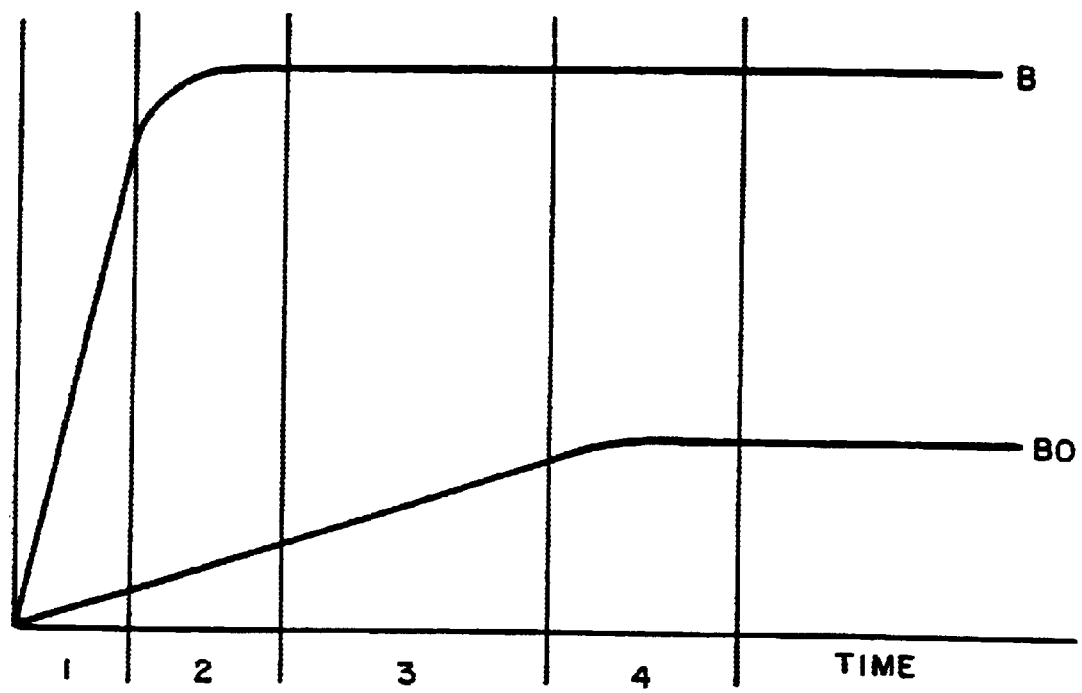
FIG. 2 shows representative binding curves for specific (B) and non-specific binding ($B_0$)

FIG. 2 shows simplified binding curves representing specific (B) and non-specific ($B_0$) binding reactions. These simplified binding curves are representative of actual binding curves that could readily be plotted by one of ordinary skill in the art using standard mathematical modelling techniques. Consistent with observation of actual binding reactions, the curves presented in FIG. 2 depict a situation in which the rate of non-specific binding, $B_0$, is lower than that of specific binding, B.

As is known in the art and shown in FIG. 2, binding curves consist of three basic regions: an approximately linear region that increases from zero (region 1 for B curve; regions 1–3 for $B_0$ curve); a curved region representing a levelling off of the binding reaction (region 2 for B curve; region 4 for $B_0$ curve); and a substantially constant region that is achieved after longer times, as the binding reaction reaches equilibrium (regions 3–5 for B curve; region 5 for $B_0$ curve).

For any particular binding curve, the slope of the approximately linear region is given by:

$$ka^*[Ab]^*[S],$$

where ka is the association rate constant and [Ab] and [S] are the concentrations of the two reactants. The slope of this region is linear only to the extent that [Ab] and [S] are constant.

At t=0, the slope of the binding curve is given by:

$$d[AbS]/dt = ka^*[Ab_o]^*[S_o] \quad (1)$$

When t approaches infinity, the value approached by the constant region of the binding curve is given by:

$$[AbS] = K^*[AB]^*[S] \quad (2)$$

where K is the equilibrium binding constant.

Thus, when comparing the two curves presented in FIG. 2, the $B/B_0$ ratios can be determined exactly for $t=0$ and for t approaching infinity:

$$\text{For } t=0, B/B_0 = k_{as}*[S_o]/k_{an}*[S_{on}] \quad (3)$$

$$\text{For } t \approx \infty, B/B_0 = K_s*[S]/K_n*[S_n] \quad (4)$$

where s represents specific binding and n represents non-specific binding.

Referring to FIG. 2, during the time period indicated as region 1, both curves are linear and the ratio $B/B_0$ is constant and of maximal value. In region 2, specific binding B levels off so that during time period of region 3, the ratio $B/B_0$ decreases as $B_0$ continues to increase. During the time period of region 4, $B_0$ levels off and the $B/B_0$ ratio assumes its lower, constant, equilibrium level.

It is apparent from reference to FIG. 2 that sandwich assays of the invention are preferably performed so that the step of contacting the second labeled binding ligand with the solid phase material is time-limited within the upper bound of region 3. That is, this step is performed such that non-specific binding levels do not have a chance to level off and the $B/B_0$ ratio does not assume its lower, constant equilibrium value.

In particularly preferred sandwich assays of the invention, this step is time-limited within the upper bound of region 2 of the graph presented in FIG. 2. Most preferably, the sandwich assays of the invention are time-limited in this step within the upper bound of region 1 of the graph of FIG. 2.

In other words, it is most desirable to perform sandwich assays of the present invention under conditions and for a time that is sufficiently limited that both the specific (i.e. second binding partner/analyte/first binding partner complex) and non-specific (i.e. second binding partner/solid phase) binding reactions are within the linear range of their respective binding curves, and have not reached equilibrium. Under such circumstances, the ratio, $B/B_0$, of specific to non-specific binding is constant.

It will also be apparent that, having temporally limited this step of the sandwich assays of the present invention within the upper bound of region 1 of the graph of FIG. 2, there is no benefit of further limiting the time of the reaction step. In fact, further decreases in reaction time are not desirable as they decrease the total amount of signal produced.

In standard sandwich assays, both the specific and non-specific binding reactions are allowed to go to equilibrium (as in region 4 and beyond of FIG. 2). Non-specific binding can contribute significantly to background reaction "noise" in such assays. Sandwich assays performed according to the methods of the invention, in which the step of contacting the second labeled binding ligand with the solid phase material is time-limited within the upper bound of region 1, 2, and/or 3 of the graph of FIG. 2, show improved sensitivity over such standard sandwich assays in which non-specific binding significantly contributes to background reaction noise.

Figure 3:
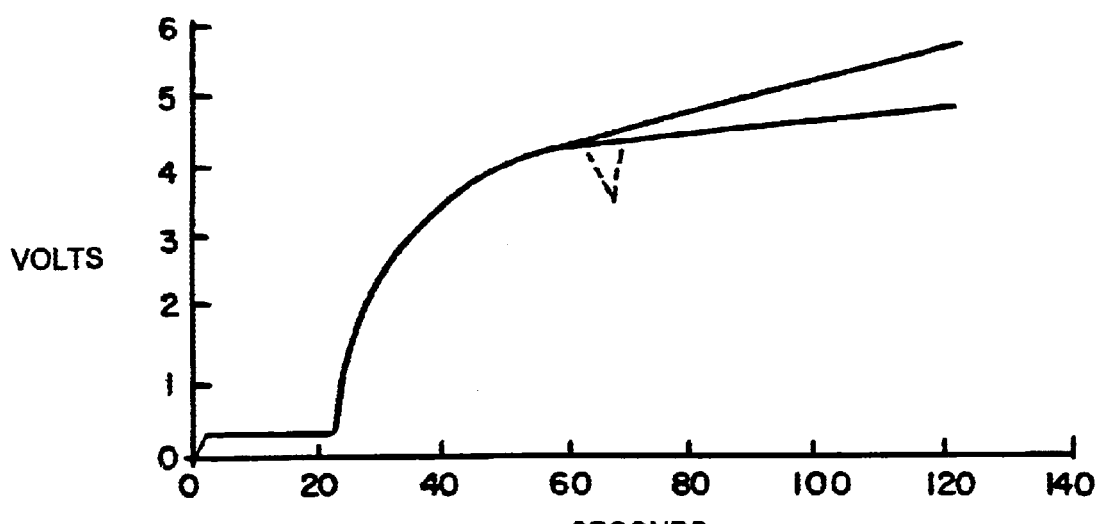
FIG. 3 shows representative output data with and without flaw.

An added benefit of the ability to monitor signal generation in real time is that it permits the establishment of "quality assurance" curves which may then be used to detect certain problems in specific assays. Although not yet fully implemented and tested, construction of quality assurance curves will be effected with the following steps:

1. The raw output data (as represented in FIG. 3 with and without air bubbles will be fit to a mathematical function, as indicated by the dashed lines. It is anticipated that the function used will depend on the particular assay and the specific timing and flow rate used. It is further anticipated that the function may consist of several functions with each covering a specified time interval. The fitting of the data to the function will be accomplished with a standard fitting algorithm such as the least squares best fit algorithm, and will vary the function parameters and get an optimal fit. The fitting algorithm will minimize the difference between the fitted function and the data set.

2. After fitting, the computer will compare the residual difference between the fitted data and function with a pre-programmed threshold value.

3. If the residual error exceeds the threshold value the computer will flag the run as flawed, or possibly, depending on the level of automation, automatically re-run it.

In the data shown, the large spike at approximately 65 on the x axis, is expected to increase the residual error enough to raise it over the threshold. The threshold value will be determined by fitting the function to large sets of both good and bad data.

Fitting to equations derived from binding kinetics should enable use of the quality assurance method to reject false positive and false negatives due to abnormally high non-specific binding. The expectation is that in the data fit the affinity constant parameter would fall outside acceptable limits.

EXAMPLE 1

In this example, a competition-like assay is performed in the method of this invention.

For the competition-like assay, the solid phase used was PMMA particles of 90 to 125 um in diameter. These particles were obtained from Bangs Laboratories, Inc., Carmel, Ind. They were adsorption coated by mixing 200 mg of particles with 1 ml of phosphate buffered saline solution (PBS) from Sigma Chemical, St. Louis, Mo., Part No. 1000-3, containing 1 mg/ml gentamicin-BSA conjugate (OEM Concepts, Toms River, N.J., Lot No. 135-68749). This mixture was incubated for 1 hour while being continuously rocked. After the 1 hour incubation, the particles were allowed to settle and the supernatant was drawn off. Next, 1 ml of a blocking solution of 10% normal goat serum (Jackson ImmunoResearch Laboratories, Inc., West Grove, Pa., Item No. 005-000-1210) was added and the particles were again rocked for 1 hour. The particles were then diluted to 30 ml in PBS and were maintained in a container.

The reaction chamber was a glass capillary with an ID of approximately 1.7 mm (Fisher Scientific, Catalog No. 21-16402J) with a 48 micrometer nylon mesh affixed approximately in the center. The reaction chamber is connected, through tubing, to computer controlled syringe pumps and valves, to accurately control the sequence and timing of the assay steps.

To perform an assay the reaction chamber is first loaded with particles in the following manner: the reaction chamber is backflushed for 30 seconds to remove any material from a prior assay. Next, 500 ul PBS is flowed forward through the reaction chamber in a period of 20 seconds. During this time a mechanical stirrer agitates the container of particles to uniformly suspend the particles. Over the next 30 seconds 750 ul of the particle containing solution is flowed through the reaction chamber, which packs about 5 mg of particles on top of the nylon mesh. This is followed by another forward PBS flow of 600 ul over 24 seconds. Next is a gentle backflush of 60 ul over 10 seconds followed by 20 seconds of no flow. This is done to allow the beads to settle by gravity to ensure a uniform bead packing. Finally a forward flow of PBS of 160 ul over 6 seconds prepares the reaction chamber for the assay.

An antibody solution is prepared as follows: mouse anti-gentamicin antibody (ImmunoPharmaceutics, Inc. San Diego, Calif. Item number 16102) is diluted to 0.1 ug/ml in PBS. 1 mg/ml BSA and 2 ug/ml FITC labeled goat anti-mouse antibody (Jackson ImmunoResearch Laboratories, Inc. West Grove, Pa. Item number 115-095-0710) is added and the solution is incubated to allow the antibodies to reach equilibrium (about 30 to 60 minutes).

Figure 4:
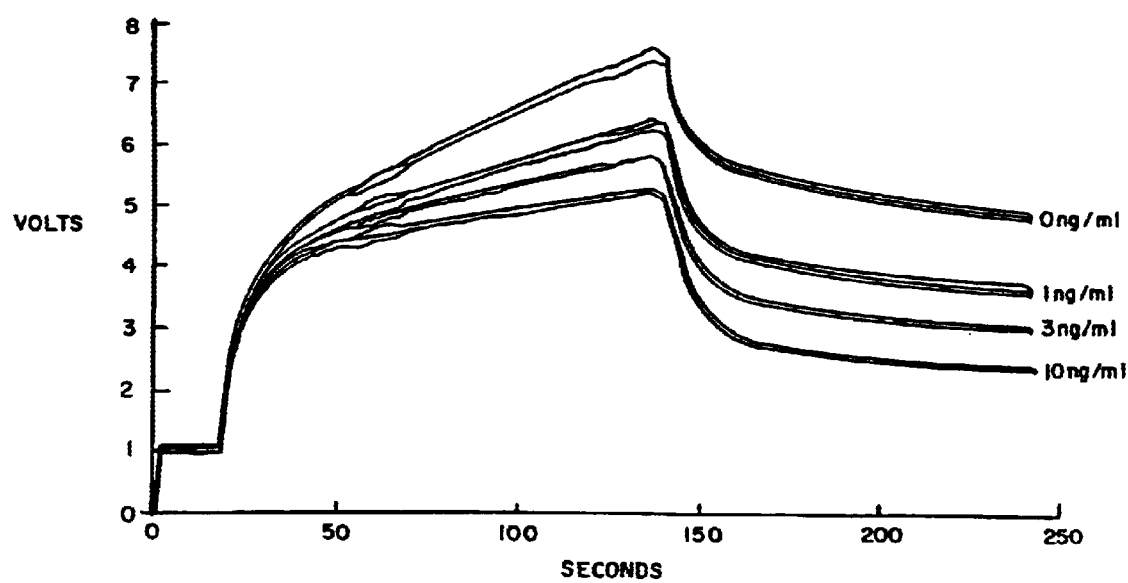
FIG. 4 shows representative family of curves for gentamicin in whole milk.

In this example the samples were whole milk spiked with gentamicin at concentrations of 0, 1, 3 and 10 ng/ml. These samples were placed on the instrument and the instrument would flow 1.5 ml of sample, while injecting an additional 1.5 ml of antibody mixture into the flow stream, through the reaction chamber over a period of 120 seconds. This was followed by 3 ml of wash over 120 seconds. The fluorescent output was monitored during the 240 seconds of sample/antibody flow and wash time. Measurements of the four samples were done in triplicate and the raw output is shown in FIG. 4.

As demonstrated in this example the preincubation time of approximately 15 seconds (the time needed to flow from the point of injection to the reaction chamber) is adequate, giving excellent sensitivity and reproducibility.

EXAMPLE 2

This example demonstrates the single point calibrator concept using undiluted label as the reference liquid. The particles are prepared using the same procedure as in example 1. After the reaction chamber is loaded with particles, antibody mixed with sample at one of three concentrations (0, 1, or 10 ng/ml) is flowed over and through the particles for 1 min at a rate of 1.5 ml/min. This is followed by a wash for 1 minute at the same rate. Next there is 40 seconds of flow of pure undiluted antibody at the same rate, giving rise to a second binding signal, which in this case is the reference. This is followed by another 1 minute wash with buffer.

Figure 5:
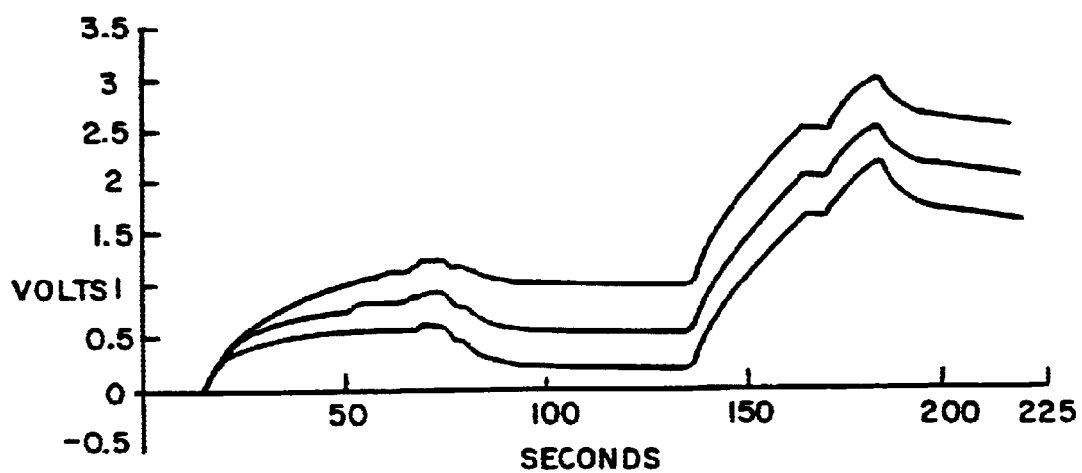
FIG. 5 shows a graph of sample and calibration signals.

FIG. 5 shows that it is possible to generate two sequential binding signals using the same solid phase. Since the second binding slopes, occurring from approximately 140 to 170 seconds and representing the reference are both reproducible and not significantly affected by the varying sample binding, occurring from approximately 25 to 70 seconds, they provide a direct measure of overall system performance.

EXAMPLE 3

A series of competition-like assay runs were made, using known concentrations of digoxin as the analyte, for the purpose of gaining a fundamental understanding of the factors that may affect sensitivity and precision using the assay methodology of this invention.

In these examples the solid phase particles were coated with digoxin-BSA (Immunotech Corp. Boston, Mass. item number 685) using a coating solution concentration of 1 mg/ml, with identical procedures as in the gentamicin example above.

A series of digoxin serum standards which are included in the commercial digoxin radioimmunoassay kits heretofore sold under the trademark "Phase II" by Binax Corporation, Portland, Me., in which the digoxin concentrations are, respectively, 0.0, 0.5, 1.0, 2.0 and 4.0 ng per ml of human serum was used as the analyte. In each instance it was diluted in a 1:4 ratio with a 1:40,000 solution in PBS of rabbit anti-digoxin unless otherwise stated below.

The primary antibody in this series of experiments was rabbit anti-digoxin at a 1:40,000 dilution in PBS unless otherwise stated below.

The secondary antibody was goat anti-rabbit immunoglobulin conjugated to fluorescein isothiocyanate at a concentration of one microgram per ml of PBS containing 0.1 percent of bovine serum albumin.

The approach adopted was to vary each of the flow rate, primary antibody concentration and analyte dilution factor while keeping the other two factors constant to the extent possible.

A set of standard conditions was chosen from which the variations were made. These conditions are:

flow rate=750 microliters per minute primary antibody concentration ("[AB]")=1:40,000 dilution analyte concentration ("[analyte]")=1:4 dilution In all of the runs the coated beads were introduced into the system in an identical manner to the gentamicin example above. After each assay the bead pack was flushed out of the tube and a new one was inserted in the same manner.

For each of these assay runs, the analyte is diluted with primary antibody solution, thereby enabling analyte and primary antibody to pre-react. The analyte dilution was introduced to the capillary conduit over a span of one minute in a volume equal to the flow rate chosen. An aliquot of 1,500 ul of secondary antibody solution was then introduced over a 120-second period and the beads were then washed with 3000 ul PBS for 120 seconds.

In the first series of experiments, sample flow rate was varied as shown in Table 1 below. It should be understood for the Table 1 runs that the total sample volume exposed to the beads is in each instance the volume introduced in one minute.

TABLE 1

Average delta values and C.V.'s for digoxin assay variable flow rate

| Flow Rate | | Digoxin Conc. (ng/ml) | | | | |
|---|---|---|---|---|---|---|
| | | 0 | 0.5 | 1 | 2 | 4 |
| 250 ul/min | Delta | 2.48 | 2.18 | 1.87 | 1.05 | 0.40 |
| | % CV | 5.0 | 4.7 | 2.9 | 3.7 | 1.5 |
| 750 ul/min | Delta | 6.09 | 5.39 | 4.63 | 3.23 | 0.75 |
| | % CV | 4.5 | 3.9 | 2.2 | 3.7 | 1.3 |
| 1500 ul/min | Delta | 6.29 | 5.37 | 4.78 | 2.58 | 0.80 |
| | % CV | 0.9 | 1.4 | 0.2 | 0.5 | 1.2 |

Figure 6:
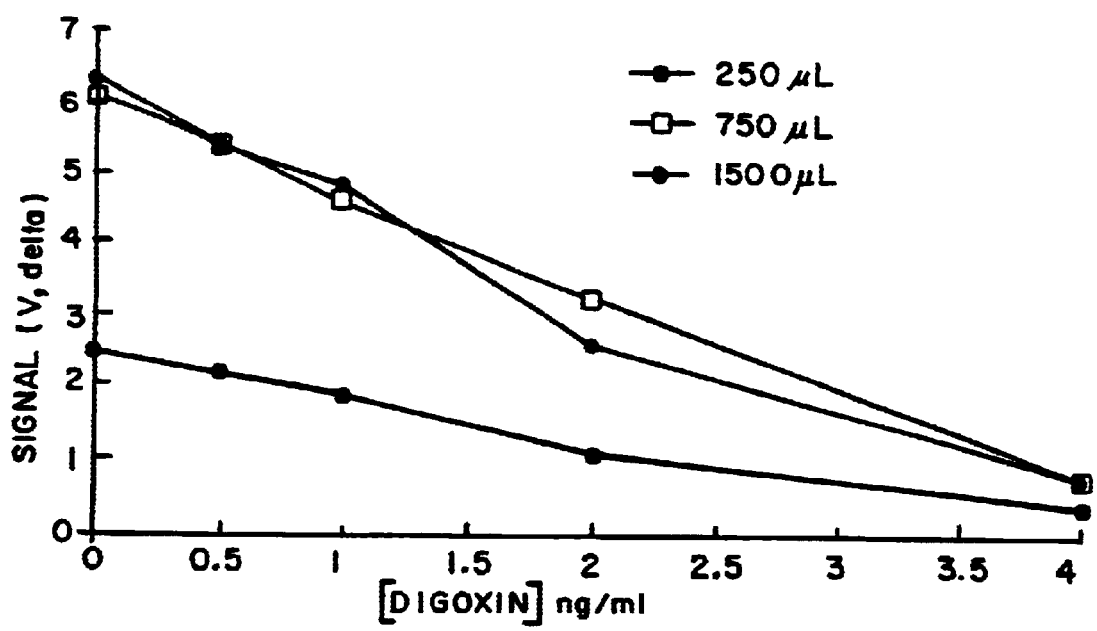
FIG. 6 shows standard curves for variable flow rate.
Figure 7:
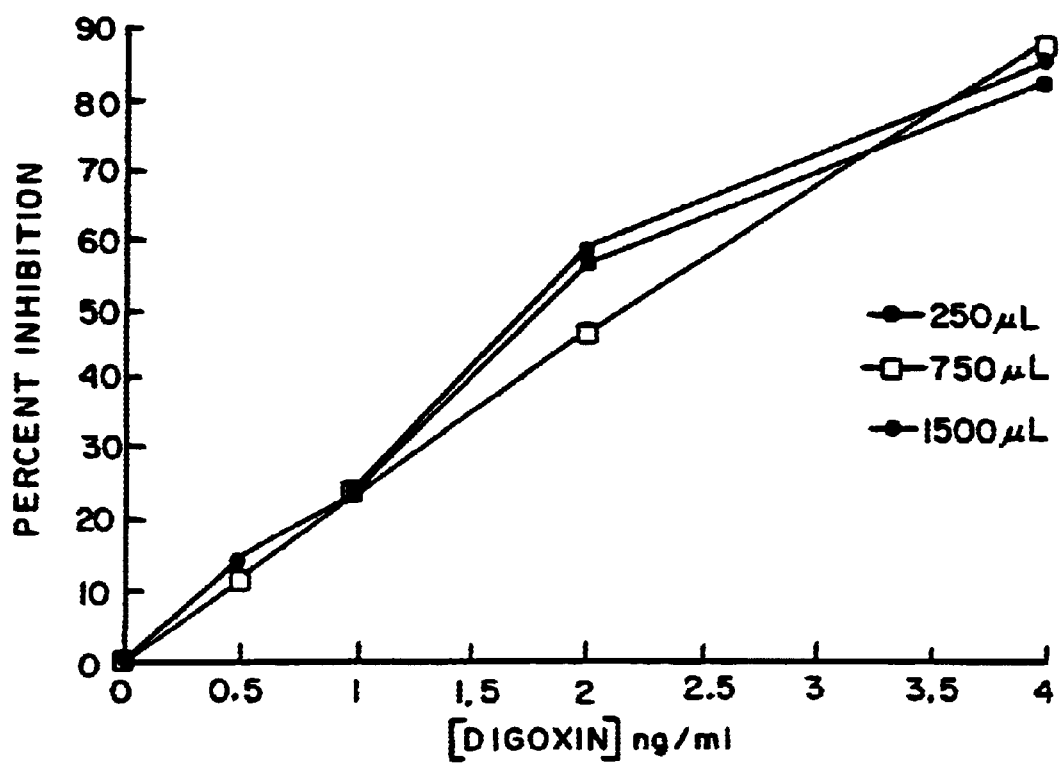
FIG. 7 shows a graph showing percent inhibition versus concentration for several flow rates.

While the Table shows the C.V. data to be best at the 1500 ul/minute flow rate, all of the C.V. data is within the 5.0% range generally considered acceptable in the art.[1] FIG. 6 shows that standard curves plotted from the variable flow rate data. As expected the change in flow rate does not affect the % inhibition curve (FIG. 7), but instead only changes the overall level, mostly due to a change in total sample/antibody used.

In the second series of experiments the dilution of primary antibody was varied as shown in Table 2 below while holding the flow rate at 750 ul per minute and the volume of sample actually utilized at 750 ul. Again, triplicate runs were made and the values given in Table 2 are the average of these.

TABLE 2

Average delta values and C.V.'s for digoxin assay variable [AB]

| Dilution of Primary Antibody | | Digoxin Conc. (ng/ml) | | | | |
|---|---|---|---|---|---|---|
| | | 0 | 0.5 | 1 | 2 | 4 |
| 1:20,000 | Delta | 6.35 | 6.31 | 6.10 | 5.28 | 3.42 |
| | % CV | 3.3 | 2.7 | 1.6 | 1.0 | 6.5 |
| 1:40,000 | Delta | 6.09 | 5.39 | 4.63 | 3.23 | 0.75 |
| | % CV | 4.6 | 3.9 | 2.2 | 3.7 | 1.3 |
| 1:100,000 | Delta | 2.87 | 1.50 | 0.86 | 0.49 | 0.37 |
| | % CV | 2.4 | 3.4 | 10.4 | 0.8 | 20.7 |

Figure 8:
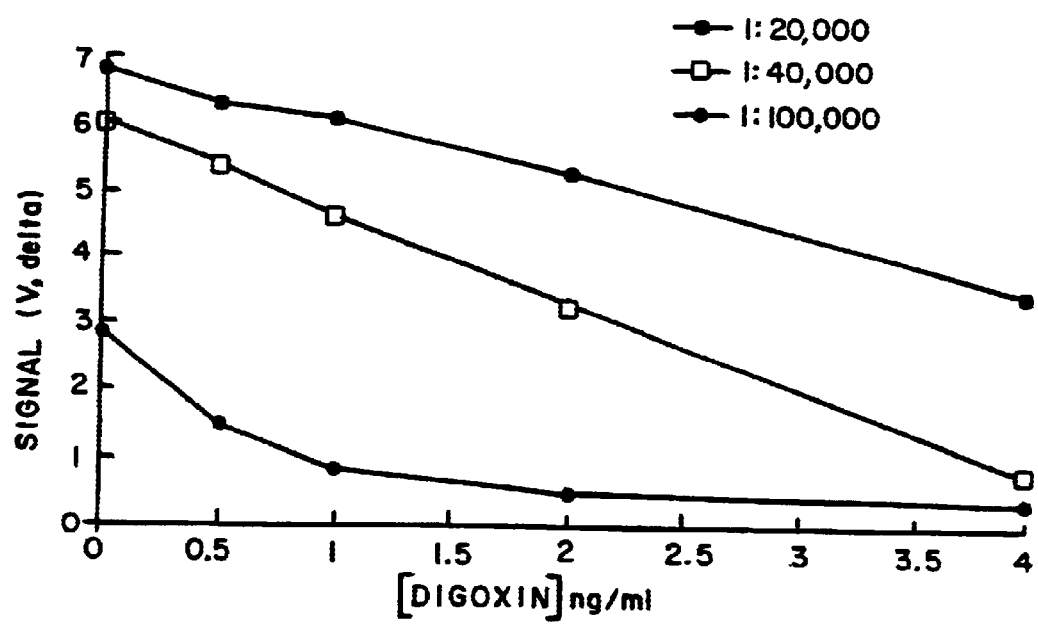
FIG. 8 shows standard curves for variable antibody dilutions.

Table 2 shows that poor coefficients of variation are obtained as complete signal inhibition is approached (as in the 1:100,000 dilution runs). FIG. 8 is a plot of the standard curves for variable primary antibody dilution and it demonstrates that, as expected, sensitivity increases as the primary antibody dilution factor increases. This is made clear by calculating the concentration of digoxin which would inhibit the signal an amount equal to 2 standard deviations from the zero concentration. For this example, 1:20,000 gives 0.494 ng/ml, 1:40,000 gives 0.392 ng/ml, and 1:100,000 gives 0.050 ng/ml.

The third series of runs, again performed in triplicate, was made to test the effect of varying the analyte dilution. It should be noted that since analyte is diluted with primary antibody solution, each change in analyte dilution factor results in a change in both analyte and primary antibody dilution even though this change has not been calculated. In all cases, the analyte solution was diluted with 1:40,000 primary antibody solution. Table 3 shows the average delta and C.V. values for each of this series of assay runs:

TABLE 3

Average delta values and C.V.'s for digoxin assay variable [Analyte]

| Analyte Dilution | | Digoxin Conc. (ng/ml) | | | | |
|---|---|---|---|---|---|---|
| | | 0 | 0.5 | 1 | 2 | 4 |
| 1:2 | Delta | 5.66 | 4.22 | 2.73 | 0.90 | 0.59 |
| | % CV | 7.0 | 2.3 | 2.5 | 5.2 | 1.8 |
| 1:4 | Delta | 6.09 | 5.39 | 4.63 | 3.23 | 0.75 |
| | % CV | 4.6 | 3.9 | 2.2 | 3.7 | 1.3 |
| 1:10 | Delta | 5.11 | 4.86 | 4.77 | 4.18 | 3.4 |
| | % CV | 3.3 | 0.6 | 3.9 | 1.9 | 2.9 |

Figure 9:
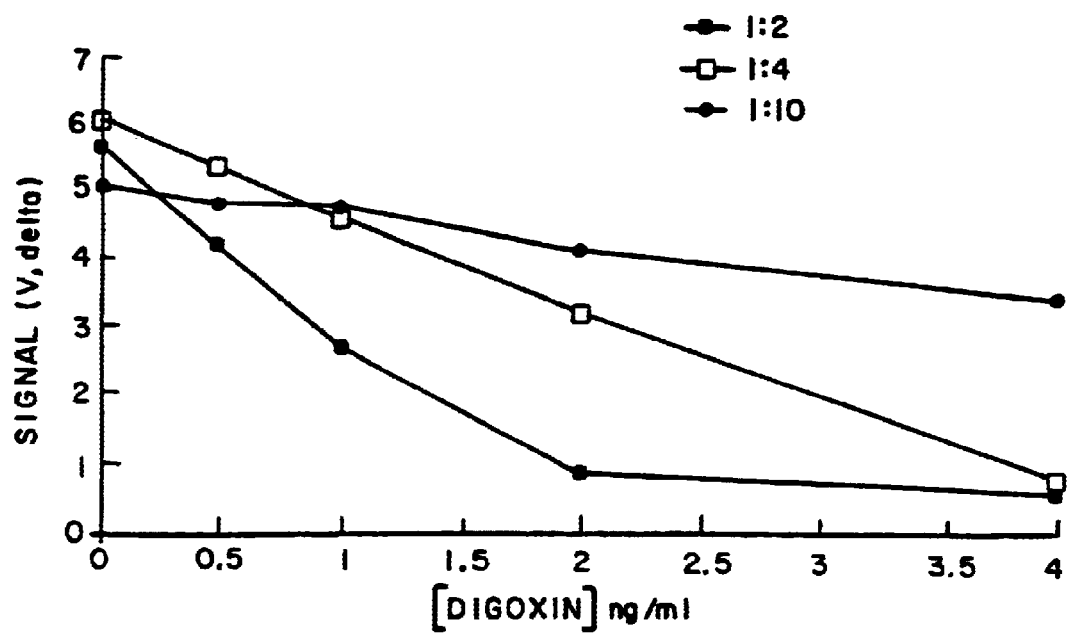
FIG. 9 shows standard curves for variable analyte dilutions.

These data exhibit C.V.'s within generally acceptable limits. FIG. 9 hereof is a plot of signal versus digoxin concentration for each of the dilution factors. It again follows our understanding in that the sensitivity increases with increasing primary antibody dilution—i.e., with decreasing free primary antibody concentration.

EXAMPLE 4

A sandwich type assay was performed with the same system as in the previous examples. The same beads identified in Example 1 were coated with sheep anti-horse ferritin of concentration 0.1 mg/ml in PBS in the manner described in Example 1. The coated beads were blocked with 10% sheep serum in PBS in the manner set forth in Example 1.

For each determination, a bead pack was established in the capillary conduit of the lens means as described in Example 1. Analyte samples were prepared by spiking a known amount of ferritin (from horse spleen) into PBS at concentration levels of 0.0 ng, 5.0 ng and 50 ng per ml of PBS.

Sheep anti-horse ferritin labelled with FITC was dissolved at 1 microgram per ml concentration in PBS containing 0.1% BSA and used as the "sandwich" antibody.

The assays were run as follows: 400 ul of analyte solution was flowed through the bead pack for 20 seconds, 750 ul of the labelled sheep anti-horse ferritin was then flowed through the bead pack for 30 seconds, followed by washing of the bead pack with 1500 ul of PBS for 60 seconds. Each of the analyte concentrations was run in duplicate. Table 4 below shows delta and slope values plus the related sigma and C.V. values for each, at all three ferritin concentrations.

TABLE 4

| Ferritin Concentration | Delta | Sigma | C.V. | Slope | Sigma | C.V. |
|---|---|---|---|---|---|---|
| 0.0 ng | 0.0754 | .0075 | 9.9% | .0513 | .0018 | 3.4% |
| 5.0 ng | 0.1475 | .0003 | 0.2% | .0539 | .0017 | 3.2% |
| 50.0 ng | 0.0348 | .0025 | 0.3% | .0775 | .0015 | 2.0% |

Figure 10A:
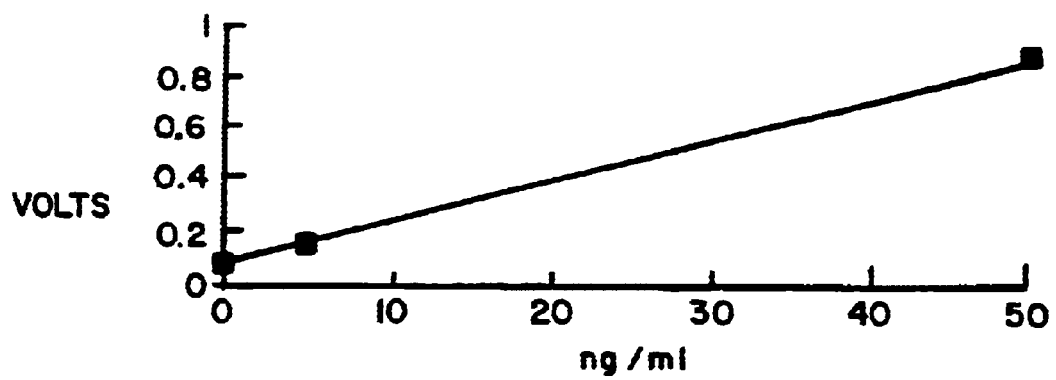
FIG. 10A and FIG. 10B show signal versus ferritin concentration.
Figure 10B:
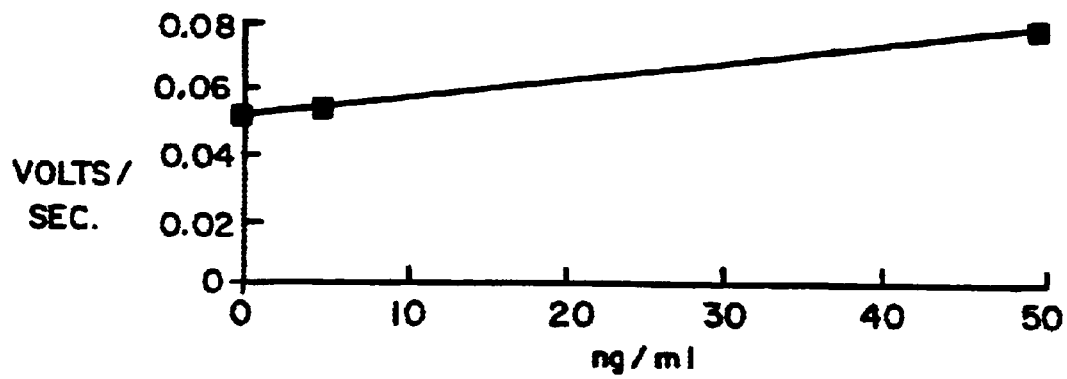

FIGS. 10A and 10B, respectively, are plot of delta signals against ferritin concentration in ng/ml and a plot of slope against ferritin concentration in ng/ml for these assays.

Example 5

A competition-like assay was run for varying concentrations of gentamicin in milk.

Beads were prepared in the manner described in Example 1. The bead pack for each assay was established using the flow rate and timing described in Example 1.

The primary and secondary antibodies were prepared by incubation for one hour at room temperature. The primary antibody, antigentamicin at a concentration of 1 microgram per ml in PBS containing 0.1% BSA was combined with secondary antibody at a concentration of 4 micrograms per ml in the same buffer solution and the incubation was allowed to proceed.

The analyte solutions were prepared by serial dilution of whole milk containing 28 ng gentamicin per ml of milk to obtain samples of concentration levels 0.0, 0.11, 0.22, 0.44, 0.88, 1.75, 3.5, 7 and 14 ng/ul gentamicin in milk. Each of these serial dilutions was combined with an equal volume of the pre-incubated primary/secondary antibody solution to perform the assay determinations.

In each assay, 1500 ul of the combined sample/antibody solution was flowed through the bead pack for 60 seconds and 3000 ul of PBS was then flowed through the beads for 120 seconds as a wash. Table 5 shows the mean delta and slope for duplicate assays, as calculated, with the sigma and C.V. of each, at all gentamicin concentration levels.

TABLE 5

| Gentamicin Concentration | Delta | Sigma | C.V. | Slope | Sigma | C.V. |
|---|---|---|---|---|---|---|
| 0.0 ng/ml | 3.0695 | 0.0991 | 3.2% | 0.0405 | 0.0011 | 2.8% |
| 0.11 ng/ml | 3.0359 | 0.0676 | 2.2% | 0.0399 | 0.0009 | 2.4% |
| 0.44 ng/ml | 2.9448 | 0.0774 | 2.6% | 0.0411 | 0.0039 | 9.4% |
| 1.75 ng/ml | 2.0841 | 0.0175 | 0.6% | 0.0371 | 0.0002 | 0.5% |
| 7.00 ng/ml | 1.4761 | 0.0200 | 1.4% | 0.0192 | 0.0003 | 1.3% |
| 0.00 ng/ml | 3.1631 | 0.0382 | 1.2% | 0.0404 | 0.0002 | 0.5% |
| 0.22 ng/ml | 3.0420 | 0.0650 | 2.1% | 0.0389 | 0.0013 | 3.3% |

TABLE 5-continued

| Gentamicin Concentration | Delta | Sigma | C.V. | Slope | Sigma | C.V. |
|---|---|---|---|---|---|---|
| 0.88 ng/ml | 2.9419 | 0.0617 | 2.1% | 0.0370 | 0.0009 | 2.3% |
| 3.50 ng/ml | 2.4352 | 0.0266 | 1.1% | 0.0305 | 0.0003 | 0.9% |
| 14.0 ng/ml | 0.3838 | 0.0050 | 1.3% | 0.0050 | 0.0001 | 23% |

The first set of 0.0 ng, 0.11 ng, 0.44 ng, 1.75 ng and 7.0 ng determinations was made on a different day from the remaining assays—hence the repeat of the 0.0 ng assays.

Figure 11A:
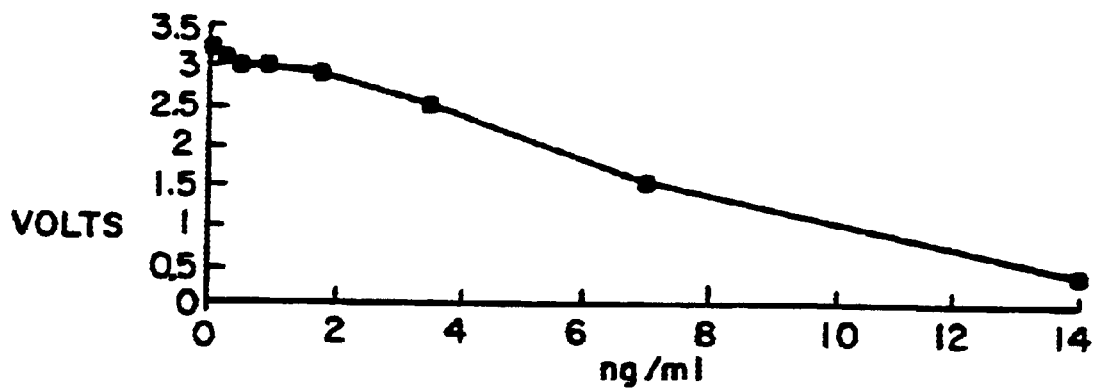
FIG. 11A and FIG. 11B show signal versus gentamicin concentration.
Figure 11B:
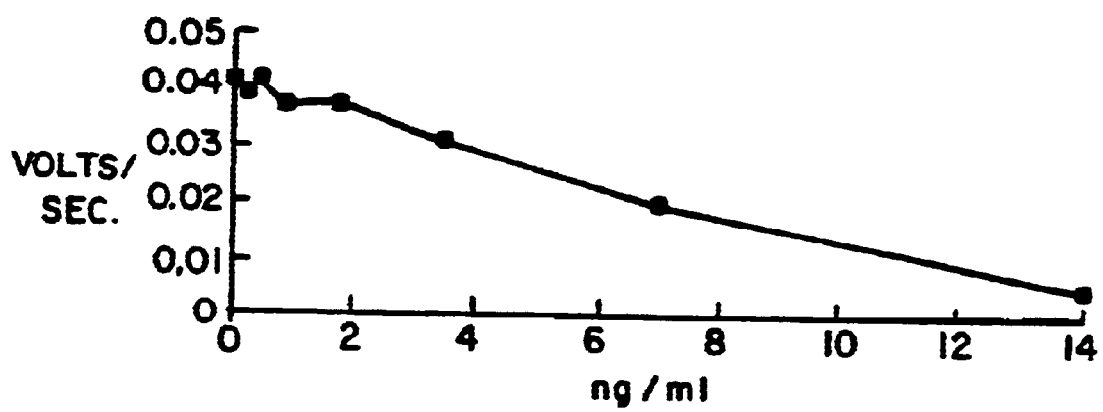

FIGS. 11A and 11B are plots, respectively, of delta signal against gentamicin in ng/ml and slope as calculated versus gentamicin in ng/ml. FIGS. 11A and 11B also provide a graphical indication of the large linear range of the "competition-like" assay system of the present invention.

EXAMPLE 6

A gentamicin single point calibrator study was made. In this study the beads were coated and blocked as described in Example 1. For each assay, a bead pack was established in the capillary conduit as described in Example 1.

The primary/secondary antibody reagent was prepared as in Example 1.

The analyte samples were prepared by serial dilution of gentamicin in whole milk to final concentrations of 0.0, 1.25, 2.5, 5.0 and 10.0 ng/ml of milk. Each was then mixed with an equal volume of the primary/secondary antibody reagent.

The reference material or calibrator was 5 ng gentamicin/ml of milk prepared in the same manner as the analyte samples.

The calibrator and analyte samples were run in the same manner which entailed flowing 1500 ul of calibrator through the beads for 60 seconds followed by flowing 1500 ul of sample containing analyte through the bead pack for 120 seconds, followed by 1500 ul of PBS for 60 seconds and then 3000 ul of PBS for 120 seconds.

Each sample was run in triplicate with calibrator and unknown in tandem each time. The mean results for slope values with associated sigma and C.V. appear in Table 6:

TABLE 6

| Sample | Slope | Sigma | C.V |
|---|---|---|---|
| Calibrator Set 1 | 0.0446 | 0.0004 | 0.9% |
| 0.0 ng/ml gentamicin | 0.0526 | 0.0308 | 1.6% |
| Calibrator Set 2 | 0.0445 | 0.0006 | 1.3% |
| 1.25 ng/ml gentamicin | 0.0512 | 0.0011 | 2.2% |
| Calibrator Set 3 | 0.0440 | 0.0009 | 2.0% |
| 2.5 ng/ml gentamicin | 0.0436 | 0.0019 | 4.4% |
| Calibrator Set 4 | 0.0446 | 0.0008 | 1.7% |
| 5.0 ng/ml gentamicin | 0.0328 | 0.0007 | 2.2% |
| Calibrator Set 5 | 0.0445 | 0.0008 | 1.7% |
| 10.0 ng/ml gentamicin | 0.0119 | 0.0005 | 3.8% |

This table again shows excellent reproducibility of the slope, independent of the sample concentration.

The preceding examples are merely illustrative of the present invention and are not intended to be limiting. Furthermore, it should be understood that the preceding is merely a detailed description of certain preferred embodiments of the present invention. It therefore should be apparent to those skilled in the art that various modifications and equivalents can be made without departing from the spirit or scope of the present invention, as set forth in the following claims.

What is claimed is:

1. A method of detecting the presence or level of an analyte in a sample, the method comprising steps of:
    (a) providing a sample containing an analyte;
    (b) mixing said sample with a second ligand, which second ligand binds to said analyte when incubated therewith, so that analyte/second ligand complexes are formed;
    (c) providing a solid phase having bound thereto a first ligand, which first ligand is characterized by an ability to bind to said second ligand in such a way that, were said first ligand and analyte exposed simultaneously to unbound second ligand, said first ligand would compete with said analyte for binding to said second ligand;
    (d) contacting the mixture produced in step (a) with said solid phase so that unbound second ligand in said mixture binds to said first ligand on said solid phase, said contacting being performed for a time sufficiently limited that substantially no dissociation of said analyte/second ligand complexes occurs while said mixture is in contact with said solid phase;
    (e) binding a detectable tag to said second ligand either prior to or after step (a), step (b), step (c), or step (d) so that a portion of said tag is retained on said solid phase upon formation of said first ligand/second ligand complex; and
    (f) detecting said portion of said tag and comparing it to an amount of tag retained on said solid phase in the presence of a known amount of analyte to determine the presence or level of said analyte in said sample.

2. The method of claim 1 wherein the step of contacting is performed for a time sufficiently limited that a plot of first ligand/second ligand complex formation versus time does not diverge substantially from an idealized plot of the same parameters, said idealized plot representing a reaction in which no dissociation of said analyte/second ligand complex formed in step (a) occurs.

3. The method of claim 1 wherein the step of contacting is performed by serially exposing increments of mixture to the solid phase, each increment being a volume of mixture that, on average, contains a single analyte/second ligand complex, the mean contact time for any one increment being limited to less than about 10 seconds.

4. The method of claim 3 wherein the step of contacting is performed so that the mean contact time for any one increment is limited to less than about 1 second.

5. The method of claim 3 wherein the step of contacting is performed so that the mean contact time for any one increment is limited to approximately one five-hundredth of a minute.

6. The method of claim 1 wherein said first ligand and said analyte are identical.

7. The method of claim 1 wherein said first ligand and said analyte are different.

8. The method of claim 7 wherein said first ligand comprises an analog of said analyte.

9. The method of claim 1 wherein the step of mixing comprises combining said sample with said second ligand in such a way that said analyte and said second ligand are present at approximately similar concentrations in said mixture.

10. The method of claim 1 wherein the step of contacting comprises contacting said mixture with a solid phase having bound thereto an amount of said first ligand in substantial excess to the amount of unbound second ligand in said mixture.

11. The method of claim 1 wherein:
the step of mixing comprises incubating said sample and second ligand together so that analyte/second ligand complexes form and the amount of unbound second ligand in said mixture is thereby reduced; and
the step of contacting comprises forming a number of first ligand/second ligand complexes on the solid phase, the number of first ligand/second ligand complexes being smaller than it would have been had said analyte/second ligand complexes not been formed in said mixture prior to said contacting step.

12. The method of claim 1 wherein:
the step of providing a solid phase comprises providing a column including a solid phase to which said first ligand is bound;
the step of contacting comprises flowing said mixture through said column; and
the step of detecting comprises detecting accumulation of said tag on said column, above a background level of tag in solution.

13. A method of detecting the presence or level of an analyte in a sample, the method comprising steps of:
(a) contacting said sample with:
(i) a solid phase having bound thereto a first ligand that binds said analyte when incubated therewith; and
(ii) a second ligand that binds said analyte when incubated therewith, the result of the two contacting steps being that a first ligand/analyte/second ligand complex is formed on said solid phase,
(b) limiting the contact time between said second ligand and said solid phase so that:
(i) non-specific binding between said second ligand and said solid phase is not allowed to reach equilibrium; and
(ii) a first binding curve, in which formation of a non-specific second ligand/solid phase complex is plotted versus time, does not level off;
(c) binding a detectable tag to said second ligand either prior to or after formation of said first ligand/analyte/second ligand complex so that a portion of said tag is retained on said solid phase upon formation of said first ligand/analyte/second ligand complex;
(d) detecting said retained tag to determine the presence or level of said analyte in said sample.

14. The method of claim 13 wherein the step of contacting comprises steps of:
(a') contacting said sample with said solid phase so that a first ligand/analyte complex is formed on said solid phase; and
(a") contacting said first ligand/analyte complex with said second ligand so that said first ligand/analyte/second ligand complex is formed on said solid phase.

15. The method of claim 13 wherein the step of contacting comprises steps of:
(a') contacting said sample with a second ligand so that an analyte/second ligand complex is formed; and
(a") contacting said solid phase with said analyte/second ligand complex so that said first ligand/analyte/second ligand complex is formed on said solid phase.

16. The method of claim 13 wherein the step of contacting comprises contacting said sample with said solid phase and with said second ligand simultaneously so that said first ligand/analyte/second ligand complex is formed on said solid phase.

17. The method of claim 13 wherein the step of limiting further comprises limiting the time of contact between said second ligand and said solid phase so that:

(iii) binding said second ligand to said analyte or to said first ligand/analyte complex does not reach equilibrium; and
(iv) a second binding curve, in which formation of said first ligand/analyte/second ligand complex is plotted versus time, does not level off.

18. The method of claim 17 wherein the step of limiting comprises limiting the time of contact between said second ligand and said solid phase so that both said first binding curve and said second binding curve are approximately linear during the period of contact.

19. The method of claim 13 wherein the step of contacting comprises contacting said sample with a solid phase having bound thereto a substantial excess of said first ligand relative to said analyte.

20. The method of claim 13 wherein the step of contacting comprises contacting said sample with a substantial excess of said second ligand relative to said first ligand/analyte complex.

21. A method of detecting formation of a first ligand/second ligand complex on a solid phase, the method comprising steps of:
(a) contacting an analyte that binds said second ligand with said second ligand so that analyte/second ligand complexes formed;
(b) providing a solid phase having bound thereto a first ligand, which first ligand is characterized by an ability to bind to said second ligand in such a way that, were said first ligand and analyte exposed simultaneously to unbound second ligand, said first ligand would compete with said analyte for binding to said second ligand;
(c) contacting said analyte/second ligand complex with said solid phase so that a first ligand/second ligand complex is formed;
(d) limiting the time of contact between said analyte/second ligand complex and said solid phase so that substantially all of the second ligand participating in analyte/second ligand complexes remains in analyte/second ligand complexes and does not participate in interactions with said first ligand;
(e) binding a detectable tag to said second ligand either prior to or after step (a), step (b), step (c), or step (d) so that a portion of said tag is retained on said solid phase upon formation of said first ligand/second ligand complex; and
(f) detecting said portion of said tag and thereby detecting the formation of said first ligand/second ligand complex on said solid phase.

22. The method of claim 21 further comprising the step of quantifying the level of said first ligand/second ligand complex on said solid phase.

23. The method of claim 22 further comprising comparing said level with a level of first ligand/second ligand complex that is formed on said solid phase in a comparison reaction wherein said second ligand is not contacted with said analyte prior to being contacted with said solid phase.

24. A method of detecting the presence or level of an analyte in a sample, the method comprising steps of:
(a) contacting said sample with:
(i) a solid phase having bound thereto a first ligand, which first ligand is characterized in that it binds to said analyte when incubated therewith, the contacting being performed so that a first ligand/analyte complex is formed on said solid phase; and
(ii) a second ligand that binds said first ligand/analyte complex when incubated therewith, so that a first ligand/analyte/second ligand complex is formed on said solid phase, said contacting being performed under conditions and for a time sufficiently limited that substantially no non-specific binding between said second ligand and said solid phase occurs;

(b) binding a detectable tag to said second ligand either prior to or after formation of said first ligand/analyte/second ligand complex so that a portion of said tag is retained on said solid phase upon formation of said first ligand/analyte/second ligand complex;

(c) detecting said retained tag to determine the presence or level of said analyte in said sample.

* * * * *

UNITED STATES PATENT AND TRADEMARK OFFICE
CERTIFICATE OF CORRECTION

PATENT NO. : 6,664,114 B1
DATED : December 16, 2003
INVENTOR(S) : Lackie et al.

It is certified that error appears in the above-identified patent and that said Letters Patent is hereby corrected as shown below:

<u>Title page,</u>
Item [*] Notice, delete "0" and insert -- 1017 --.

Signed and Sealed this

Twenty-seventh Day of April, 2004

JON W. DUDAS
*Acting Director of the United States Patent and Trademark Office*